United States Patent [19]

Lazer et al.

[11] Patent Number: 5,296,486
[45] Date of Patent: Mar. 22, 1994

[54] LEUKOTRIENE BIOSYNTHESIS INHIBITORS

[75] Inventors: Edward S. Lazer, Trumbull; Julian Adams, Ridgefield; Clara K. Miao, Trumbull, all of Conn.; Peter Farina, North Salem, N.Y.

[73] Assignee: Boehringer Ingelheim Pharmaceuticals, Inc., Ridgefield, Conn.

[21] Appl. No.: 937,315

[22] Filed: Sep. 4, 1992

Related U.S. Application Data

[63] Continuation-in-part of Ser. No. 704,591, May 23, 1991, abandoned.

[51] Int. Cl.$^5$ .................. C07D 413/12; C07D 417/12; A61K 31/44
[52] U.S. Cl. .................................... 514/333; 514/338; 546/256; 546/270
[58] Field of Search ............... 546/270, 256; 514/333, 514/338

[56] References Cited

U.S. PATENT DOCUMENTS 4,814,459  3/1989  Boesenberg et al. .................. 71/90

OTHER PUBLICATIONS

Advani et al. J. Pharm. Sci. 57 (10) pp. 1693–1696 (1968).
Kaupp et al. Chem. Ber. 119 (5) pp. 1525–1539 (1986).

*Primary Examiner*—C. Warren Ivy
*Assistant Examiner*—Phyllis G. Spivack
*Attorney, Agent, or Firm*—D. E. Frankhouser; A. R. Stempel; M-E. M. Timbers

[57] ABSTRACT

Various substituted benzoxazoles, benzothiazoles, oxazolopyridines and thiazolopyridines are described and disclosed, compounds that are potent inhibitors of leukotriene synthesis in warm-blooded animals.

10 Claims, No Drawings

LEUKOTRIENE BIOSYNTHESIS INHIBITORS

This is a continuation-in-part of prior U.S. application Ser. No. 764,591 filed Sep. 24, 1991, now abandoned.

Leukotrienes (LTs) are potent, pro-inflammatory substances that are produced in the metabolism of arachidonic acid. It is believed that LTs play a role in various inflammatory diseases, such as asthma, allergic rhinitis, rheumatoid arthritis, inflammatory bowel disease and psoriasis. Accordingly, inhibition of the biosynthesis of LTs has potential utility in the treatment of diseases in which inflammation and arachidonic acid metabolism have been implicated.

The biosynthesis of leukotrienes and their pathophysiology have been well documented. Many investigators have been seeking to block the pathophysiological effects of leukotrienes either by blocking their biosynthesis or by blocking their activity at the receptor level. Two recent reviews (J. H. Musser and A. F. Kreft, J. Med. Chem. 1992, 35,2501 and A. Shaw and R. D. Krell, J. Med. Chem. 1991, 34, 1235) describe the status of research in these areas, including results of clinical trials. Results of clinical trials such as those cited in these articles support the concept that agents that block the biosynthesis or activity of leukotrienes will be useful in asthma and possibly other inflammatory diseases mentioned above.

This invention relates to various substituted benzoxazoles, benzothiazoles, oxazolopyridines and thiazolopyridines which have the ability to inhibit leukotriene biosynthesis. Such compounds have the general formula:

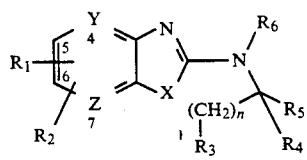

Formula I wherein
X is O or S;
Y is C or N;
Z is C or N;
with the proviso that Y and Z are not both N; $R_1$ and $R_2$ are each, independent of one another, hydrogen; $C_1$-$C_6$ alkyl; halo; $CF_3$; nitrile; $C_1$-$C_6$ alkoxy; —$CO_2R_7$ wherein $R_7$ is hydrogen or $C_1$-$C_6$ alkyl; —C(O)$NR_8R_9$ wherein $R_8$ and $R_9$ are hydrogen, $C_1$-$C_3$ alkyl, methoxy or together with N form a morpholine, pyrrolidine or piperidine ring; —$NO_2$; —$NR_{10}R_{11}$ wherein $R_{10}$ and $R_{11}$ are hydrogen or $C_1$-$C_6$ alkyl; —C(O)$R_{12}$ wherein $R_{12}$ is $C_1$-$C_6$ alkyl; —$SO_2R_{12}$; —NHC(O)$R_{12}$; —$NHSO_2R_{12}$; or —$SO_2NR_{13}R_{14}$ wherein $R_{13}$ and $R_{14}$ hydrogen or $C_1$-$C_6$ alkyl.

$R_3$ is cycloehyxyl or an unsubstituted or substituted pheny ring wherein the substituents are selected from halo, $CF_3$, $C_1$-$C_4$ alkyl and $C_1$-$C_4$ alkoxy; $SO_2R_{12}$; —NHC(O)$R_{12}$, —$NHSO_2R_{12}$; —$SO_2NR_{13}R_{14}$or $NO_2$; or $R_3$ may be a 1-piperidinyl ring, a 2-, 3- or 4- pyridine ring, a morpholine ring, a thiomorpholine ring, a pyrrolidine ring, an imidazole ring optionally substituted on nitrogen with $C_1$-$C_4$ alkyl, or a 2-thiazole ring or a 2-methyl-4-thiazole ring; $R_3$ may also be a dialkylamine ($C_1$-$C_4$) or an alkyl ether ($C_1$-$C_4$).

$R_4$ is an ester of structure —$CO_2R_{16}$ wherein $R_{16}$ is $C_1$-$C_4$ alkyl; or an amide of structure —C(O)$NR_{17}R_{18}$ wherein $R_{17}$ and $R_{18}$ are hydrogen, $C_1$-$C_3$ alkyl, methoxy or together with N form a morpholine ring, or together with N form a piperidine or pyrrolidine ring; an unsubstituted or substituted phenyl ring wherein the substituents are selected from halo, $C_1$-$C_4$ alkyl or $C_1$-$C_4$ alkoxy; a 3-methyl-1,2,4-oxadiazol-5-yl group; a 2- or 3-thienyl group; or a 2-, 3-, or 4-pyridyl group; a 2-imidazole group optionally substituted on N with a methyl group; a 2-thiazole group optionally substituted on the 4-position with a methyl; a ketone of structure C(O)$R_{19}$ wherein $R_{19}$ is $C_1$-$C_3$ alkyl, phenyl, or 1-methylimidazol-2-yl; an ether—$CH_2OR_{20}$ where $R_{20}$=$C_1$-$C_3$ alkyl, a thioether, —$CH_2SR_{20}$; a sulfone,—$CH_2SO_2CH_3$; an amine, —$CH_2NHSO_2Me_2$; or a carbamate, —$CH_2OC(O)NHMe$;

$R_5$ and $R_6$ are independently of each other hydrogen or methyl; and
n is an integer 0, 1 or 2.

Such compounds may be in racemic form, or the pure or substantially pure enantiomers may be isolated. The preferred compounds are those wherein the $R_1$ substituent is in the 5-position and is an $C_1$-$C_3$ alkyl group or halogen, the $R_3$ substituent is cyclohexyl, the $R_6$ substituent is hydrogen and n is 1.

In J. Pharm. Sci (57, p. 1695) by S. Advani and J. Sam (1968) four compounds are disclosed having a basic structure like that of Formula I. The Advani publication, a publication on potential anti-neoplastic agents, discloses synthesis of these four compounds, but no biological activity is provided. In the Advani publication, Y and Z are both carbon, $R_4$ is —$CO_2C_2H_5$, $R_1$ and $R_2$ are both hydrogen and $R_3$ is 4—$C_6H_4OH$, —$C_6H_5$, 4-imidazolyl or —$CH_2SCH_3$.

In Ger. Off. DE 3419994 there are described compounds of general formula I wherein both Y and Z are C, X is O or S, $R_1$ and $R_2$ are hydrogen, halo, $C_1$-$C_4$ alkyl, $C_1$-$C_4$ alkoxy, CN, $NO_2$ or $CF_3$, $R_4$ is —C(O)$OR_{16}$, (wherein $R_{16}$, is hydrogen, alkyl, alkenyl or alkynyl), —C(O)N($R_{18}$)($R_{19}$) (wherein $R_{18}$ and $R_{19}$ are hydrogen, $C_1$-$C_6$ alkyl, phenyl or alkoxy or together with N form a pyrrolidine, piperidine or morpholine ring), —CN or —C(S)$NH_2$. The group referred to as "Y" in such Ger. Off. DE 3419994 consists of $R_3$ and the carbon chain, i.e., $(CH_2)_n$ shown in Formula I. The groups at "Y" disclosed in such German publication are straight-chain or branched alkyl ($C_1$-$C_8$, with one to three carbons between N and $R_4$, or the group designated "Z" in such published application, methylthioalkyl (one to three carbons in the alkyl) or phenylalkyl. Specifically not disclosed at $R_3$ is a cyclohexyl group or substituted phenyl. Also, not disclosed at $R_4$ are ketones or phenyl and heteroaromatic or publication is Y or Z being nitrogen. At $R_6$ the German publication discloses hydrogen and $C_1$-$C_4$ alkyl. Specifically not disclosed are the preferred compounds of the present invention. Compounds disclosed in the German publication are said to be useful for protecting crops against certain classes or types of herbicides.

The compounds of the present invention may be prepared by methods and processes known in the art and published in the literature. For example, compounds may be prepared by reaction of an appropriately substituted 2-chlorobenzoxazole, 2-chlorobenzothiazole, 2-chlorooxazolopyridine or 2-chlorothiazolopyridine with an amine, an amino acid or an amino acid ester. Such synthesis scheme is outlined herein below as Scheme A.

Scheme A

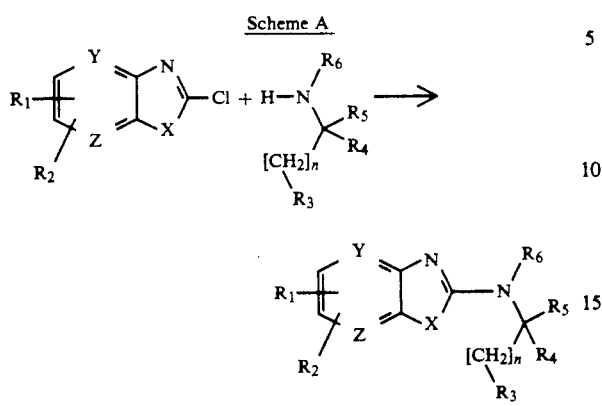

The reaction of Scheme A may occur in an inert solvent, such as methylene chloride, toluene or DMSO, with a basic catalyst, such as triethylamine or NaOH. The optimum choice of both solvent and catalyst will depend on the nature of the reactants, as a person skilled in the art would recognize.

Alternatively, modification of a procedure known in the literature for preparation of 2-aminobenzothiazoles may be successfully employed for synthesis of compounds of general formula I. Such synthesis scheme is outlined hereinbelow as Scheme B.

Scheme B

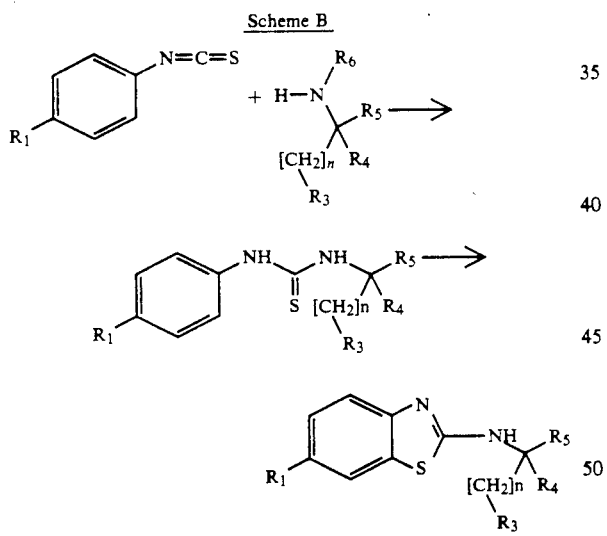

The procedure of Scheme B involves reaction of an appropriately substituted isothiocyanate with an amine or an amino acid ester in a suitable inert solvent, such as ether, followed by cyclization of the intermediate thiourea with sulfuryl chloride or bromine in another inert solvent, again such as ether or perhaps chlorobenzene.

Scheme C

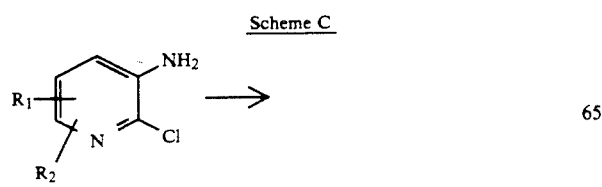

Scheme C -continued

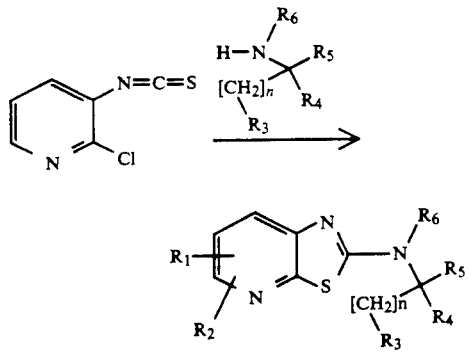

The synthesis of Scheme C can be employed for those compounds of general formula I wherein X is S and Z is N. A haloaminopyridine is converted to an isothiocyanate, for example by reaction with thiophosgene, in the presence of a base, such as sodium carbonate, in an inert solvent. Treatment of the isothiocyanate with an amine in an inert solvent yields a thiazolopyridine. With certain additional substituents on the 2-chloro-3-aminopyridine ring, an intermediate thiourea is isolated upon reaction with the isothiocyanate. In that case, cyclization to the thiazolopyridine product may be accomplished by heating in an inert solvent with either acid or base catalysis, for example in ethanolic HCl or DMF with $K_2CO_3$.

Isomeric thiazolopyridines may be prepared by cyclization of a 3-halo-2-thiourea substituted pyridine. Such a synthetic scheme is outlined hereinbelow as Scheme D.

Scheme D

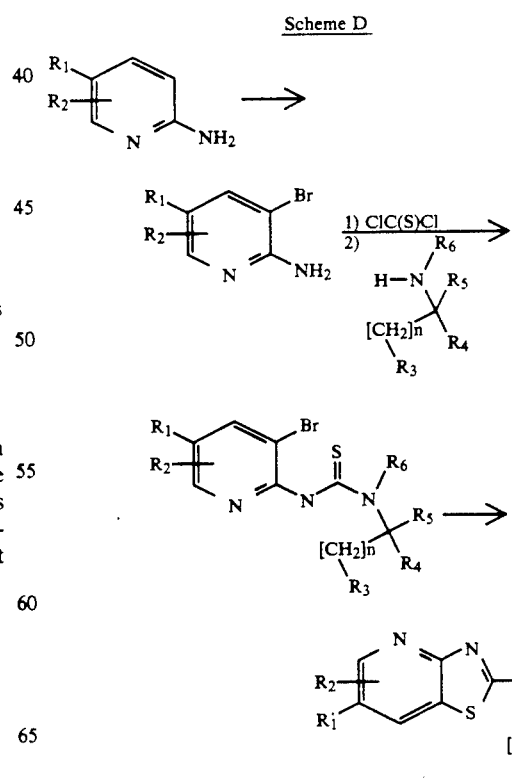

In Scheme D, the 3-halo-2-thiourea pyridine is heated in an inert solvent with base catalysis, for example $K_2CO_3$ in DMF. The intermediate 2-amino-3-halopyridine may be prepared, for example, by bromination of an optionally substituted 2-aminopyridine. The isothiocyanate may be prepared as described in Scheme C.

Compounds of general formula I wherein $R_4$ is an acid or an ester may be modified to yield compounds of general formula I is an amide, a methyloxadiazole a ketone an ether, or thioether. The scheme for such modification is shown hereinbelow Scheme E.

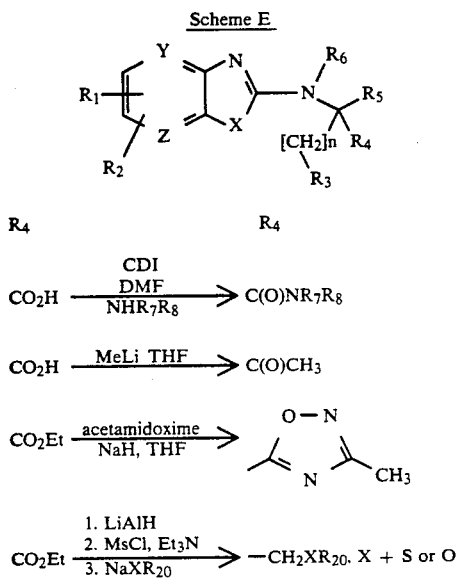

Scheme E

All the general methods exemplified in Scheme E are well known to one skilled in the art, and are also published in the chemical literature.

Concerning the stereochemistry of compounds produced via the methods and schemes outlined hereinabove, if the starting amines used in Schemes I and II above are enantiomerically pure, then a single enantiomer of the end product, having either R or S configuration at the asymmetric carbon, will be recovered. By the same token, if the starting amine is racemic, that is, a mixture of R and S, then a racemic end product will be recovered. Racemic compounds may be separated into the individual enantiomers by methods known to one skilled in the art, for example, by resolution of a diastereomeric salt, chromatography on a chiral column, etc. In the text of this specification the designation for enantiomers of amino acids D and L, or racemic DL, will be used.

The following examples are illustrative of the present invention. Such examples, however, are not to be construed as limiting the scope of the present invention, which scope is defined in the claims which follow. As would be obvious to one skilled in the art, other compounds, such as where $R_4$ is pyrrolidine-amide, can be readily synthesized using the methods and procedures outline above.

EXAMPLE 1

DL-N-(Benzothiazol-2-yl)phenylalanine hydrochloride 11.8 g phenylalanine (71.4 mmol) was added in portions to a suspension of 5.7 g powdered NaOH (143 mmol) in 50 mL DMSO, and stirred under nitrogen. 2-Chlorobenzothiazole (11 g, 65 mmol) was added over fifteen minutes at room temperature. The reaction was heated on an oil bath at about 95° C. for 4 hours. The reaction mixture was then cooled, poured into 200 mL ice and water, and the pH of the resulting mixture was adjusted to about 1-2 by addition of 10N HCl.

More ice was added, and the mixture was then stirred and filtered. The white solid was dissolved in alkaline solution, stirred with celite, filtered, acidified with 2N HCl and filtered. The resulting solid was rinsed with water, then EtOH, and dried. The product (6.47 g, 19.3 mmol, 30%) melted at 250°-251° C.

EXAMPLE 2

DL-N-(Benzothiazol-2-yl)phenylalanine ethyl ester Compound No. 4. Table 1

Thionyl chloride (3.82 g, 32.1 mmol) was added dropwise to the product from Example 1 (3.2 g, 10.7 mmol) suspended in 200 mL EtOH. The reaction was heated at reflux for four hours. The reaction mixture was then concentrated, the residue dissolved in EtOAc (75 mL) and extracted with saturated $Na_2CO_3$ solution (2×50 mL), saturated NaCl solution (50 mL) dried ($Na_2SP_4$) and concentrated. The product was recrystallized from EtOH giving 2.25 g (6.9 mmol, 64%) mp 137°-139° C.

EXAMPLE 3

DL-N-(6-Isocrocylbenzothiazol-2-yl)-4-chlorophenylalanine ethyl ester

Compound No. 7, Table 1

DL-4-Chlorophenylalanine ethyl ester hydrochloride(5 g, 18.9 mmol) was converted to the free base using triethylamine. A solution of the free base in 75 mL ether was added to a solution of 4-isopropylphenylisothiocyanate in 150 mL ether, cooled on an ice-salt bath. The temperature was maintained at about 0° C. during addition. The reaction was stirred for four and one-half hours, at which time the reaction temperature was 12° C.. The reaction mixture was filtered, the filtrate concentrated, and the resulting foamy residue triturated with petroleum ether while cooling on ice. This resulted in 6.1 g (15.1 mmol, 80%) N-(4-isopropylphenyl)-N'-[2-(4-chlorophenyl)-1-(ethoxycarbonyl)ethyl]thiourea, mp 73°-75° C.

The intermediate product (6 g, 14.8 mmol) was dissolved in 25 mL chlorobenzene and cooled on an ice bath to 0° C.. Sulfuryl chloride (2.76 g, 20.4 mmol) in 5 mL chlorobenzene was added dropwise. After five and one-half hours, the reaction mixture was concentrated, the residue dissolved in EtOAc (150 mL), washed with saturated $Na_2CO_3$ solution, then saturated NaCl solution, dried ($Na_2SO_4$) and concentrated. The product crystallized from EtOH, giving 4.07 g(10.1 mmol, 68%), mp 105°-107° C.

EXAMPLE 4

2-(2-Cyclohexyl-1-phenyl)ethylaminobenzoxazole

Compound No. 51, Table 3

A mixture of 1.12 g 2-chlorobenzoxazole (7.3 mmol), 1.48 g 2-cyclohexyl-1-phenylethylamine (7.3 mmol) and 0.88 g triethylamine (8.8 mmol) in 305 mL $CH_2Cl_2$, was refluxed for 31 hours. The reaction mixture was diluted with 50 mL $CH_2Cl_2$, extracted with water (1×50 mL), 1N HCl (1×50 mL), saturated NaCl (1×50 mL), dried ($Na_2SO_4$ and concentrated. The resulting solid was recrystallized from EtOH giving 1.4 g product (4.4 mmol, 60%) mp 129°-131° C.

EXAMPLE 5

L-2-2-Cyclohexyl-1-(3-methyl1,2,4-oxadiazol-5-methyl-benzoxazole

Compound No. 125, Table 6

0.47 g 60% NaH in mineral oil dispersion (0.28 g NaH, 11.8 mmol), 0.39 g acetamidoxime (5.3 mmol), 1.48 g N-(5-methylbenzoxazol-2-yl)cyclohexylalanine methyl ester (4.7 mmol), and several molecular sieves were combined in 20 mL THF and refluxed for two hours under nitrogen. The mixture was poured into water and extracted with EtOAc. The EtOAc was dried ($Na_2SO_4$) and concentrated. The product was purified by flash chromatography on silca gel (99 $CH_2CH_2$:1 MeOH). After triturating with petroleum ether the product was obtained as a white solid, 70 mg, mp 118°-119° C.

EXAMPLE 6

(5-Methylbenzoxazol-2-cyclohexylalanine-N'-methylamide

Compound No. 44, Table 2

A solution of 1.08 g L-N-(5-methylbenzoxazol-2-yl)cyclohexylalanine (3.6 mmol) in 15 mL $CH_2Cl_2$ was cooled on an ice bath. Carbonyldiimidazole (0.88 g, 5.4 mmol) was added in portions. After one hour methylamine gas was bubbled into the reaction mixture for about forty-five minutes. The reaction was diluted with $CH_2Cl_2$, washed with water, saturated NaCl solution, dried ($Na_2SO_4$) and concentrated. The product was purified by flash chromatography on silica gel, eluting with 99 $CH_2Cl_2$:1 MeOH, followed by recrystallization from isopropanol giving 0.2 g product, m.p. 202°-204° C.

EXAMPLE 7

3-[(6-Isopropylbenzothiazol-2-yl)amino]-4-phenylbutan-2-one

Compound No. 128, Table 7

A solution of 2 g N-(6-isopropylbenzothiazol-2-yl)phenylalanine (5.9 mmol) in 60 mL THF was cooled on an ice-salt bath to −5° C., under nitrogen. A solution of 1.4 N MeLi in ether (26 mL, 36.4 mmol) was added via syringe over about one minute. After two hours 10 mL chlorotrimethylsilane (78 mmol) was added rapidly and the reaction warmed up to room temperature. The reaction was quenched with 1N HCl and the product extracted into ether, dried ($Na_2SO_4$) and concentrated. The product was purified by flash chromatography thru silica gel, eluting with $CH_2Cl_2$. Recrystallization from EtOH gave 0.75 g product (2.2 mmol, 38%), mp 107°-110° C.

EXAMPLE 8

-[(2-Cyclohexyl-1-phenylethyl)amino]thiazolo[5,4-b]pyridine

Compound No. 172, Table 11

A mixture of 1.28 g (10 mmol) 3-amino-2-chloropyridine, 2.1 g (20 mmol) sodium carbonate and 1.38 g (12 mmol) thiophosgene in 50 mL $CH_2Cl_2$ was stirred overnight at room temperature. The reaction mixture was poured into water, and extracted with $CH_2Cl_2$. The combined organic extracts were washed with saturated NaCl solution, dried ($Na_2SO_4$) and concentrated to give an oil. The product was purified by chromatography on silica gel, eluting with petroleum ether, giving 1.6 g thioisocyanate (9.4 mmol, 94%).

The thioisocyanate (0.516 g, 3.02 mmol) was added to a mixture of 0.66 g 2-cyclohexyl-1-phenylethylamine hydrochloride (2.75 mmol), and 0.278 g triethylamine (2.75 mmol) in 25 mL THF. The reaction was heated at reflux for two hours, poured into water, and extracted with ether. The organic extracts were washed with saturated NaCl solution, dried ($MgSO_4$) and concentrated. Recrystallization of the residue from $CH_2Cl_2$-petroleum ether gave 0.625 g product (1.84 mmol, 67%) mp 146°-148° C.

EXAMPLE 9

2-{[2-Cyclohexyl-1-(2-pyridyl)ethyl]amino}-6-methyl-thiazolo-(4,5-b]pyridine

Compound No. 184, Table 11

Bromine (3.19 g) was added dropwise at 0° C. to a solution of 2-amino-5-picoline in 75 mL $CH_2Cl_2$. After about two hours at room temperature, the reaction was extracted with saturated sodium carbonate solution, then sodium thiosulfate solution. The combined aqueous extracts were washed with $CH_2Cl_2$, and the combined organic extracts washed with saturated NaCl, dried ($Na_2SO_4$) and concentrated giving 3.59 g crude material. The product was purified by flash chromatography on silica gel, eluting with petroleum ether with increasing amounts of $CH_2Cl_2$ (0–40%), giving 3.05 g 2-amino-3-bromo-5-picoline, m.p. 68°-70° C.

To the above product (2.84 g, 15 mmol) in 50 mL $CH_2Cl_2$ with 3.18 g (30 mmol) sodium carbonate, was added 2.07 g (18 mmol) thiophosgene. After stirring overnight at room temperature, the reaction was extracted with water, the aqueous phase back extracted with $CH_2Cl_2$ and combined organic extracts washed with brine, dried ($MgSO_4$), and concentrated giving the isothiocyanate as an oily material that crystallized on standing (3.9 g) IR 2050 cm$^{-1}$.

To a solution of 1.0 g (4.3 mmol) of the isothiocyanate derivative and 1.04 g (4.3 mmol) of 2-cyclohexyl-1-phenylethylamine in 50 ml dry THF was added 438 mg (4.3 mmol) of $Et_3N$. The resulting mixture was refluxed for two hours. The triethylamine hydrochloride was filtered off and the filtrate concentrated to give the thiourea (1.6 g) which crystallized on standing.

A mixture of 540 mg (1.15 mmol) of the thiourea and 317 mg (2.3 mmol) $K_2CO_3$ in 10 mL DMF was refluxed overnight. The reaction mixture was then poured into water and extracted with ether(3×) and $CH_2Cl_2$ (1×). The organic extracts were washed with brine, dried ($Na_2SO_4$) and concentrated giving 450 mg product. Recrystallization from $CH_2Cl_2$/ether/petroleum ether gave 210 mg product, m.p. 213°-214° C.

Inhibition of LTB$_4$, biosynthesis in human polymorphonuclear leukocytes (PMNs)

The inhibition of leukotriene biosynthesis is measured by determining whether and to what extent test compounds can inhibit LTB$_4$ production from endogenous arachidonic acid in human peripheral blood leukocytes.

To 48-well tissue culture plates was added a solution of the test compound followed by addition of human polymorphonuclear leukocytes isolated from peripheral blood at a density of 1.5×10$^6$ cells/well. Culture plates were preincubated for fifteen minutes with shaking at 28° C. Cells were stimulated with calcium ionosphere A23187 at a final concentration of 2.5 μM for an additional ten minutes. The reaction was terminated by the addition of an EGTA solution (10 mM final concentration) followed by centrifugation at 1500 rpm at 10° C. Supernatants were stored at −70° C. LTB$_4$ levels were determined by RIA using a commercially available kit. Nonlinear regression analysis was used to calculate IC50 values.

The following tables show % inhibition of LTB$_4$ biosynthesis by compounds of the invention at test concentrations indicated, with the determined IC$_{50}$ shown in μM.

TABLE 1
Esters

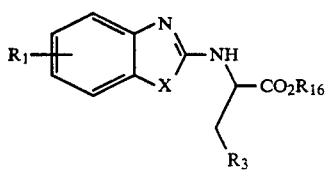

| Comp No. | D/L[a] | R$_1$ | R$_3$[b] | R$_{16}$ | X | mp | IC$_{50}$ (μM) |
|---|---|---|---|---|---|---|---|
| 1 | DL | H | Ph4Cl | Et | S | Oil | 0.2 |
| 2 | DL | H | Ph4F | Et | S | 129-131 | 0.33 |
| 3 | DL | H | Ph4Br | Et | S | 104-106 | 0.15 |
| 4 | DL | H | Ph | Et | S | 137-139 | 0.4 |
| 5 | L | H | Ph4OBZ | Et | S | Oil | 0.53 |
| 6 | L | 6-iPr | Ph | Et | S | Oil | 0.25 |
| 7 | DL | 6-iPr | Ph4Cl | Et | S | 105-107 | 0.33 |
| 8 | L | 6-iPr | Ph | Me | S | 114-115 | 0.14 |
| 9 | DL | 6-OMe | Ph4Cl | Et | S | 129-131 | 0.23 |
| 10 | D | 6-iPr | Ph | Me | S | 115-116 | 0.65 |
| 11 | DL | 6-nBu | Ph4Cl | Et | S | 113-114 | 0.17 |
| 12 | L | 6-Et | Ph | Et | S | 102-104 | 0.24 |
| 13 | L | H | Ph | t-Bu | S | 50-52 | 0.73 |
| 14 | L | 5-Et | Ph | Et | S | Oil | 0.009 |
| 15 | L | 5-Et | Cyh | Et | S | Oil | 0.027 |
| 16 | L | H | Cyh | Et | S | resin | 0.006 |
| 17 | L | H | Ph | Et | O | Oil | 0.15 |
| 18 | D | H | Ph | Et | O | Oil | 1.5 |
| 19 | L | 5-iPr | Ph | Et | O | Oil | 0.00052 |
| 20 | L | 6-iPr | Ph | Et | O | Oil | 0.22 |
| 21 | L | H | Cyh | Me | O | Oil | 0.0064 |
| 22 | D | H | Cyh | Me | O | Oil | 0.10 |
| 23 | L | 5-iPr | Cyh | Me | O | Oil | 0.001 |
| 24 | L | 5-Me | Cyh | Me | O | Oil | 0.0017 |
| 25 | L | 5-Me | Cyh | t-Bu | O | Oil | <0.3[d] |
| 26 | D | 5-Me | Cyh | Me | O | Oil | 0.016 |
| 27 | DL | 5-OMe | 2Me4Thz | Et | O | Oil | <0.3[d] |
| 28 | DL | 5-Cl | 2-Thz | Et | O | Oil | <0.3[d] |
| 29 | DL | 5-Cl | 2Me4Thz | Et | O | Oil | 0.087 |
| 30 | DL | 5-iPr | 3-Py | Et | O | Oil | 0.19 |
| 31 | DL | 5-iPr | 4-Py | Et | O | Oil | <0.1[d] |
| 32 | DL | 5-OMe | 3-Py | Et | O | Oil | |
| 33 | DL | 5-iPr | 2Me4Thz | Et | O | Oil | <0.03[d] |

TABLE 1A
Esters

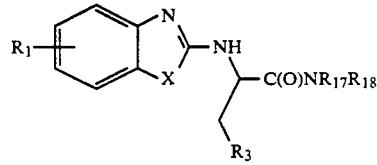

| Comp No. | D/L | R$_6$ | R$_5$ | R$_{3'}$ | n | x | mp | IC$_{50}$ (μM) |
|---|---|---|---|---|---|---|---|---|
| 34 | DL | H | H | CH$_3$ | 0 | S | Oil | 1.4 |
| 35 | DL | H | H | CH$_3$ | 0 | S | Oil | 0.68 |
| 36 | DL | CH$_3$ | H | H | 0 | S | Oil | 1.0 |
| 37 | DL | H | H | H | 1 | S | 69.5-72 | 0.52 |
| 38 | DL | H | CH$_3$ | H | 0 | S | 97-98 | 0.20 |
| 39 | DL | H | CH$_3$ | H | 0 | O | 89-91.5 | 0.076 |

Footnotes (for TABLES 1 and 1A)
[a]DL = racemic. L or D indicates one enantiomer with stereochemistry at chiral carbon analogous to the corresponding L or D amino acid.
[b]Ph = phenyl, PhX = substituted phenyl, Cyh = Cyclohexyl 2-Thz = 2-Thiazolyl, 2Me4Thz = 2-methyl-4-thiazolyl, 3-Py = 3-pyridyl, 4-Py = 4-pyridyl
[c]One of a pair of diastereomers
[d]Greater than 50% inhibition at this concentration, IC$_{50}$ not characterized further.

TABLE 2
Ester Bioisosteres - Amides

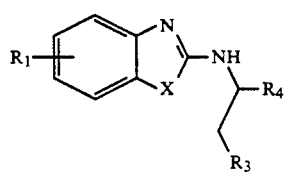

| Comp No. | D/L | R$_1$ | R$_3$[a] | R$_{17}$ | R$_{18}$ | x | m.p. °C. | IC$_{50}$ (μM) |
|---|---|---|---|---|---|---|---|---|
| 40 | L | H | Ph | H | H | S | 94-96 | 3 |
| 41 | DL | H | Ph | Me | Me | S | Oil | 3 |
| 42 | DL | 6-iPr | Ph | Et | H | S | 161-163 | 3 |
| 43 | L | H | Ph | Me | OMe | O | Resin | <1[c] |
| 44 | L | 5-Me | Cyh | Me | H | O | 202-204 | 0.072 |
| 45 | L | 5-Me | Cyh | Me | OMe | O | Resin | 0.03 |
| 46 | L | 5-Me | Cyh | b | b | O | Resin | 0.19 |

[a]See footnote b, Table 1.
b R$_{17}$ and R$_{18}$ with nitrogen make a piperidine ring.
[c]See footnote d, Tables 1 and 1A.

TABLE 3
Ester Bioisosteres - Phenyl

| Comp. No. | D/L[a] | R$_1$ | R$_3$[b] | R$_4$[b] | X | m.p. °C. | IC$_{50}$ (μM) |
|---|---|---|---|---|---|---|---|
| 47 | DL | H | Ph | Ph | S | 54-56 | 0.16 |

TABLE 3-continued

Ester Bioisosteres - Phenyl

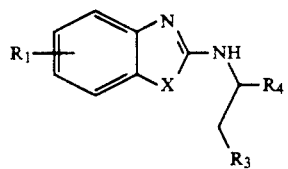

| Comp. No. | D/L[a] | $R_1$ | $R_3$[b] | $R_4$[b] | X | m.p. °C | IC$_{50}$ (μM) |
|---|---|---|---|---|---|---|---|
| 48 | 'L' | H | Ph | Ph | S | Oil | 0.082 |
| 49 | 'D' | H | Ph | Ph | S | Oil | 0.28 |
| 50 | DL | H | Ph | Ph | O | 154-156 | <1.0[d] |
| 51 | DL | H | Cyh | Ph | O | 129-131 | 0.0069 |
| 52 | 'D' | H | Cyh | Ph | O | 141-143 | 0.26 |
| 53 | 'L' | H | Cyh | Ph | O | 135.5-137 | 0.0036 |
| 54 | DL | 5-iPr | Cyh | Ph | O | 119-122 | 0.0063 |
| 55 | DL | H | Cyh | Ph4Cl | O | 142-144 | 0.3 |
| 56 | DL | H | Cyh | Ph4OMe | O | 63-67 | 0.55 |
| 57 | DL | H | Cyh | Ph3Me | O | 136-138 | 0.30 |
| 58 | DL | H | Cyh | Ph2Cl | O | 146-148 | 0.08 |
| 59 | DL | 5-I | Cyh | Ph | O | 186-187 | 0.013 |
| 60 | DL | 5-NHSO$_2$—CH$_3$ | Cyh | Ph | O | 188-190 | 0.16 |
| 61 | DL | 5-NHC(O)CH$_3$ | Cyh | Ph | O | 145-147 | 0.076 |
| 62 | DL | 5-NHC(O)NHCH$_3$ | Cyh | Ph | O | 211-212 | <1.0[d] |
| 63 | DL | 5-CO$_2$H | Cyh | Ph | O | 232-234 | 0.19 |
| 64 | DL | 5-C(O)NH$_2$ | Cyh | Ph | O | 181-183 | <1.0[d] |
| 65 | DL | 5-C(O)NMe$_2$ | Cyh | Ph | O | 194-196 | 0.17 |
| 66 | DL | 6-CO$_2$H | Cyh | Ph | S | 271-272 | 0.22 |
| 67 | DL | 5-CN | Cyh | Ph | O | 166-168 | 0.15 |
| 68 | DL | C | Cyh | Ph | O | 154-156 | <1.0[d] |
| 69 | DL | CH$_2$OH | Cyh | Ph | O | 187-189 | <1.0[d] |
| 70 | DL | 5-tetrazolyl | Cyh | Ph | O | 188-191 | 0.16 |
| 71 | DL | H | Cyh | Ph4F | O | 144-145 | 0.17 |
| 72 | L | 5-Cl | NEt$_2$ | Ph | O | 242-244 | 0.35 |
| 73 | L | 5-iPr | NnPr$_2$ | Ph | O | Oil | <300[d] |
| 74 | L | 5-iPr | OEt | Ph | O | Oil | 0.11 |
| 75 | L | 5-iPr | OnBu | Ph | O | Oil | 0.055 |
| 76 | L | 5-tBu | morph | Ph | O | 197-199 | <0.03[d] |
| 77 | L | 5-iPr | NEt$_2$ | Ph | O | Oil | <0.3[d] |
| 78 | L | 5-Cl | thiomorph | Ph | O | 69-71 | 0.048 |

[a]DL = racemic. 'L' and 'D' = L = isomer designation based on potency being greater than 'D' isomer, and drawing analogy to esters where L and D are known.
[b]See footnote b, Table 1, also morph = N-morpholinyl, thiomorph = N-thiomorpholinyl.
[c]morpholinecarbonyl
[d]See Footnote d, Table 1.

TABLE 4

Ester Bioisosteres - Pyridyl

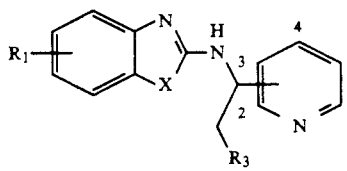

| 79 | D/L | X | $R_1$ | $R_3$[a] | Pyridyl Isomer | mp °C | IC$_{50}$ (μM) |
|---|---|---|---|---|---|---|---|
| 80 | DL | O | H | Cyh | 3 | Resin | 0.055 |
| 81 | DL | O | 5-Me | Cyh | 2 | 104-105 | 0.0031 |
| 82 | DL | O | 5-Me | Cyh | 3 | 150-151 | 0.024 |
| 83 | DL | O | 5-Me | Cyh | 4 | 188-189 | 0.19 |
| 84 | DL | O | 6-NO$_2$ | Cyh | 3 | 186-187.5 | 0.035 |
| 85 | DL | O | 5-NO$_2$ | Cyh | 3 | 189-190 | 0.024 |
| 86 | DL | O | 5-Cl | Cyh | 3 | 186-187 | 0.023 |
| 87 | (−)* | O | 5-Me | Cyh | 2 | Oil | 0.0013 |
| 88 | (+)* | O | 5-Me | Cyh | 2 | Oil | 0.045 |
| 89 | (−)* | O | 5-Me | Cyh | 3 | 150-151 | 0.016 |
| 90 | (+)* | O | 5-Me | Cyh | 3 | 150-151 | <1.0 |
| 91 | DL | O | 5-Cl | Cyh | 2 | 132-134 | 0.002 |
| 92 | DL | O | 5-CO$_2$Me | Cyh | 2 | 129-131 | 0.012 |
| 93 | DL | O | 5-Cl | Ph4F | 2 | 112-114 | 0.019 |
| 94 | DL | O | 5-iPr | Ph4F | 2 | 56-58 | 0.012 |

TABLE 4-continued
Ester Bioisosteres - Pyridyl

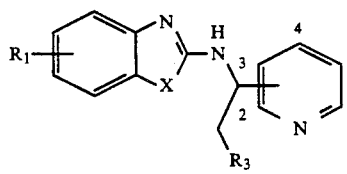

| 79 | D/L | X | R₁ | R₃$^a$ | Pyridyl Isomer | mp °C. | IC$_{50}$ ($\mu$M) |
|---|---|---|---|---|---|---|---|
| 95 | DL | O | 5-CF₃ | Cyh | 2 | 91-93 | 0.0012 |
| 96 | DL | S | 5-Cl | Ph4F | 2 | 133-135 | 0.027 |
| 97 | DL | S | 5-Cl | Cyh | 2 | 129-132 | 0.004 |
| 98 | DL | O | 5-iPr | Ph4Cl | 2 | 65-67 | 0.029 |
| 99 | DL | O | 5-Cl | Ph4Cl | 2 | 132-134 | 0.014 |
| 100 | DL | O | 5-iPr | Ph3Cl | 2 | 51-52 | 0.005 |
| 101 | DL | O | 5-CO₂Me | Ph4F | 2 | 151-152 | 0.027 |
| 102 | DL | S | 5-Cl | Cyh | 2 | 129-132 | 0.004 |
| 103 | DL | O | 5-SO₂NMe₂ | Ph4F | 2 | 178-179 | 0.050 |
| 104 | DL | O | 5-Cl | Ph4NO₂ | 2 | 72-74 | <0.03$^b$ |
| 105 | DL | O | 5-F | Ph3Cl | 2 | 131-133 | <0.03$^b$ |
| 106 | DL | S | 6-CF₃ | Ph4F | 2 | 149-150 | <1.0$^b$ |
| 107 | DL | O | 5-CF₃ | Ph4F | 2 | 105-107 | 0.008 |
| 108 | DL | O | 5-CF₃ | Cyh | 2 | 91-93 | 0.001 |
| 109 | DL | O | 5-F | Cyh | 2 | 142-143.5 | 0.002 |
| 110 | DL | O | 5-F | Ph4F | 2 | 117-119.5 | 0.021 |
| 111 | DL | O | 4,5-diF | Cyh | 2 | 133-134 | 0.004 |
| 112 | DL | O | 5,6-diF | Cyh | 2 | 131-133 | 0.001 |
| 113 | DL | O | 5,6-diF | Ph4F | 2 | 143-144.5 | 0.024 |
| 114 | DL | O | 5-OMe | Ph4F | 2 | 111-113 | 0.011 |
| 115 | DL | O | 5-NO₂ | Ph4F | 2 | 174-175 | <0.03$^b$ |
| 116 | DL | O | 5-iPr | 2Me4Thz | 2 | 116-117 | <0.1$^b$ |
| 117 | DL | O | 5-Cl | 2Me4Thz | 2 | 142-143 | <0.1$^b$ |
| 118 | (−)* | O | 5-Cl | Ph4F | 2 | Oil | 0.01 |
| 119 | (+)* | O | 5-Cl | Ph4F | 2 | Oil | 0.32 |

*(−) and (+) refer to the levorotatory and dextrorotatory enantiomer respectively. Enantiomers were separated by HPLC on a Chiralcel OD column eluting with hexane:i-PrOH:Et₂NH 950:50:1.
$^a$See footnote b, Table 1.
$^b$See footnote d, Table 1.

TABLE 5
Ester Bioisosteres - Thiophene

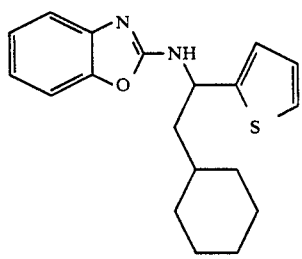

| Comp. No. | D/L | mp °C. | IC$_{50}$ ($\mu$M) |
|---|---|---|---|
| 120 | DL | 108-110 | 0.0062 |

TABLE 6
Ester Bioisosteres - Methyloxadiazole

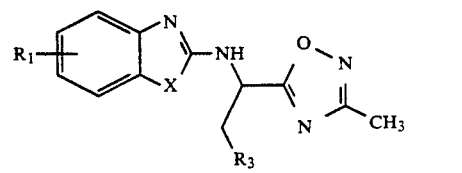

| Comp. No. | D/L | R₁ | R₃$^a$ | X | mp °C. | IC$_{50}$ ($\mu$M) |
|---|---|---|---|---|---|---|
| 121 | DL | H | Ph | S | 122-124 | 1.3 |
| 122 | L | H | Ph | S | 117-119 | 1.8 |
| 123 | L | 5-Et | Ph | S | 134-136 | <1.0$^b$ |
| 124 | L | H | Cyh | S | 147-149 | 0.12 |
| 125 | L | 5-Me | Cyh | O | 118-119.5 | 0.028 |
| 126 | DL | 5-iPr | Ph4F | O | 86 | <0.3$^b$ |
| 127 | DL | 5-iPr | 2Me4Thz | O | 45-48 | <1.0$^b$ |

$^a$See footnote b, Table 1.
$^b$See footnote d, Table 1.

TABLE 7

Ester Bioisosteres - Ketones

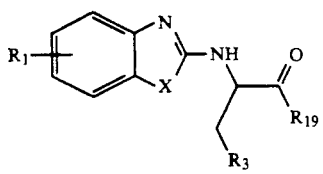

| Comp. No. | D/L | R$_1$ | R$_3^a$ | R$_{19}$ | X | mp °C. | IC$_{50}$ ($\mu$M) |
|---|---|---|---|---|---|---|---|
| 128 | L | 6-iPr | Ph | CH$_3$ | S | 107-110 | 0.35 |
| 129 | L | H | Ph | CH$_3$ | O | Oil | <1.0 |
| 130 | L | H | Ph | Ph | O | Resin | <0.3 |
| 131 | L | 5-Me | Cyh | Ph | O | Resin | <1.0 |
| 132 | L | 5-Me | Cyh | b | O | Resin | 0.023 |

$^a$See footnote b, Table 1.
b 1-methyl-2-imidazolyl

TABLE 8

Ester Bioisosteres - Miscellaneous Acyclic

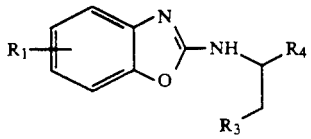

| Comp. No. | D/L | R$_1$ | R$_3^a$ | R$_4$ | mp °C. | IC$_{50}$ ($\mu$M) |
|---|---|---|---|---|---|---|
| 133 | L | 5-iPr | Ph | CH$_2$OEt | Oil | 0.016 |
| 134 | L | 5-iPr | Ph | CH$_2$OPr | Oil | 0.22 |
| 135 | L | 5-Cl | Ph | CH$_2$OEt | Oil | 0.029 |
| 136 | DL | 5-iPr | Ph4F | CH$_2$OMe | Oil | <0.03$^b$ |
| 137 | DL | 5-iPr | Ph4F | CH$_2$OEt | Oil | <0.03$^3$ |
| 138 | DL | 5-iPr | Ph4F | CH$_2$OnPr | Oil | <0.3$^b$ |
| 139 | DL | 5-iPr | Ph4OMe | CH$_2$OMe | Oil | <0.03$^b$ |
| 140 | DL | 5-iPr | 3-Py | CH$_2$OMe | Oil | <1.0$^b$ |
| 141 | DL | 5-iPr | 2Me4Thz | CH$_2$OMe | Oil | <0.3$^b$ |
| 142 | L | 5-iPr | Ph3Cl | CH$_2$SMe | Oil | <0.03$^b$ |
| 143 | DL | 5-iPr | 3-Py | CH$_2$SMe | Oil | <1.0$^b$ |
| 144 | DL | 5-iPr | 4-Py | CH$_2$SMe | Oil | |
| 145 | DL | 5-iPr | 2Me4Thz | CH$_2$SMe | Oil | <0.1$^b$ |
| 146 | DL | 5-iPr | Ph | CH$_2$SO$_2$Me | resin | <0.03$^b$ |
| 147 | DL | 5-iPr | 3-Py | CH$_2$SO$_2$Me | 88-92 | <1.0$^b$ |
| 148 | DL | 5-iPr | 4-Py | CH$_2$SO$_2$Me | 78-81 | |
| 149 | DL | 5,6-diF | Ph4F | CH$_2$SO$_2$Me | 179-181 | |
| 150 | L | 5-iPr | Ph | CH$_2$NMe$_2$ | Oil | <0.3$^b$ |
| 151 | L | 5-iPr | Ph | CH$_2$NHC(O)Me | resin | <0.1$^b$ |
| 152 | L | 5-iPr | Ph | CH$_2$NHSO$_2$NMe$_2$ | resin | <0.1$^b$ |
| 153 | L | 5-iPr | Ph | CH$_2$NHC(O)NH$_2$ | resin | <0.3$^b$ |
| 154 | L | 5-iPr | Ph | CH$_2$OC(O)NHMe | 125-126 | 0.063 |

$^a$See footnote b, Table 1
$^b$See footnote d, Table 1

TABLE 9

Ester Bioisosteres: Miscellaneous Heterocycle

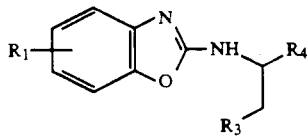

| Comp. No. | D/L | R$_1$ | R$_3^a$ | R$_4^b$ | mp °C. | IC$_{50}$ ($\mu$M) |
|---|---|---|---|---|---|---|
| 155 | DL | 5-Cl | Ph4F | 2-Imid | 248-250 | 0.29 |
| 156 | DL | 5-iPr | Ph4F | 2-Imid | 213-219 | 0.09 |
| 157 | DL | 5-iPr | 2-Me4Thz | 2-Imid | 153-155 | <1.0$^c$ |
| 158 | DL | 5-iPr | Ph3Cl | 2-Imid | 210-213 | <0.03$^c$ |
| 159 | DL | 5-iPr | Ph3Cl | 2-Thz | resin | <0.1$^c$ |
| 160 | DL | 5-iPr | Ph3Cl | 4Me2Thz | resin | <0.03$^c$ |

TABLE 9-continued

Ester Bioisosteres: Miscellaneous Heterocycle

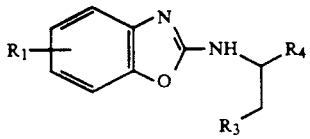

| Comp. No. | D/L | R$_1$ | R$_3^a$ | R$_4^b$ | mp °C. | IC$_{50}$ ($\mu$M) |
|---|---|---|---|---|---|---|
| 161 | DL | 5-iPr | Ph | 4-Pyraz | 206-210 | <0.1$^c$ |

$^a$See footnote b, Table 1.
$^b$2-Imid = 2-imidazolyl, 2-Thz = 2-thiazolyl, 4Me2Thz = 4-methyl-2-thiazolyl, 4-Pyraz = 4-pyrazolyl
$^c$See footnote d, Table 1.

TABLE 10

Oxazolopyridines

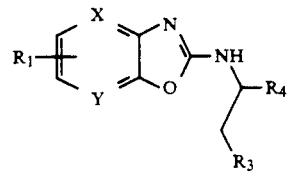

| Comp. No. | D/L | X | Y | R$_1$ | R$_3^a$ | R$_4^a$ | mp °C. | IC$_{50}$ ($\mu$M) |
|---|---|---|---|---|---|---|---|---|
| 162 | L | N | C | H | Cyh | CO$_2$Me | 147-149 | 0.21 |
| 163 | DL | N | C | H | Cyh | Ph | 189-190.5 | 0.078 |
| 164 | DL | N | C | 5-Me | Cyh | Ph | 199-200 | 0.028 |
| 165 | DL | N | C | 5-Me | Cyh | 2-Py | 134- | 0.026 |

TABLE 10-continued
Oxazolopyridines

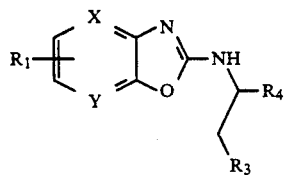

| Comp. No. | D/L | X | Y | R₁ | R₃[a] | R₄[a] | mp °C. | IC₅₀ (μM) |
|---|---|---|---|---|---|---|---|---|
| 166 | (−)* | N | C | 5-Me | Cyh | 2-Py | 136 68–75 | 0.015 |
| 167 | (+)* | N | C | 5-Me | Cyh | 2-Py | 68–75 | 0.17 |
| 168 | DL | N | C | 5-Me | Cyh | 3-Py | 207–208 | 0.3 |
| 169 | DL | N | C | 5-Me | Ph4F | 2-Py | 66–69 | <0.3[b] |
| 170 | DL | C | N | H | Cyh | Ph | 133–134 | 0.021 |
| 171 | DL | C | N | 5-Me | Cyh | Ph | 188–191 | 0.044 |

[a]See footnote b Table 1. Also 2-Py - 2-pyridyl, 3-Py = 3-pyridyl.
[b]See footnote d, Table 1.
*See * Table 4.

TABLE 11
Thiazolopyridines

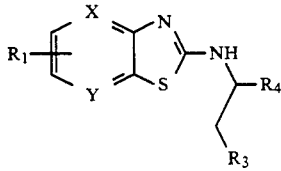

| Comp. No. | DL | X | Y | R₁ | R₄[b] | R₃[b] | mp °C. | IC₅₀ (μM) |
|---|---|---|---|---|---|---|---|---|
| 172 | DL | C | N | H | Ph | Cyh | 146–148 | 0.027 |
| 173 | DL | C | N | H | 3-Py | Cyh | 222–224[a] | 0.17 |
| 174 | DL | C | N | H | 2-Py | Cyh | 176–178[a] | 0.027 |
| 175 | DL | C | N | 5-Me-6-Br | 2-Py | Cyh | 215–217 | 0.009 |
| 176 | DL | C | N | 5-Me | 2-Py | Cyh | 109–113 | 0.01 |
| 177 | DL | C | N | 5-Me | 3-Py | Cyh | 174–175.5 | 0.11 |
| 178 | DL | C | N | 6-Cl | 3-Py | Cyh | 207–209 | 0.044 |
| 179 | DL | C | N | 6-Cl | 2-Py | Cyh | 180–182 | 0.006 |
| 180 | DL | C | N | 4-Me | 2-Py | Cyh | 144–146 | <1.0[c] |
| 181 | DL | C | N | 6-Cl | 3-Py | Cyh | 207–209 | 0.044 |
| 182 | DL | C | N | 6-Cl | 2-Py | Ph4F | 151–153 | 0.110 |
| 183 | DL | C | N | 5-Cl | 2-Py | Ph4F | 146–149 | 0.280 |
| 184 | DL | N | C | 6-Me | 2-Py | Cyh | 214–216 | 0.031 |
| 185 | DL | N | C | 5-Me-6-Br | 2-Py | Cyh | 209–210 | 0.0065 |
| 186 | DL | N | C | 5-Me-6-Br | 3-Py | Cyh | 241–243.5 | 0.021 |
| 187 | DL | N | C | 5-Me | 2-Py | Cyh | 167–171 | 0.013 |
| 188 | DL | N | C | 6-Cl | 2-Py | Cyh | 198.5–200.5 | 0.0039 |
| 189 | DL | N | C | 6-Cl | 2-Py | Ph4F | 204–205 | 0.028 |
| 190 | DL | C | N | 5-Me-6-Br | 3-Py | Cyh | 211–212 | <1.0[c] |
| 191 | DL | N | C | 6-Me | Ph | Cyh | 213–214 | <1.0[c] |
| 192 | DL | N | C | 6-Me | 2-Py | Ph4F | 184–185 | <0.3[c] |

[a]Hydrochloride salt.
[b]See footnote b Table 1. Also 2-Py = 2-pyridyl, 3-Py = 3-pyridyl.
[c]See footnote d, Table 1.

TABLE 12
Miscellaneous Compounds

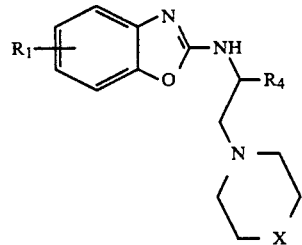

| Comp. No. | DL | R₁ | R₄ | X | mp °C. | IC₅₀ (μM) |
|---|---|---|---|---|---|---|
| 193 | L | 5-iPr | Ph[b] | C | 165[a] | 0.1 |
| 194 | L | 5-Me | Ph | C | >150[a] | 0.23 |
| 195 | L | 5-iPr | 2-Py | C | 128 | 0.19 |
| 196 | L | 5-iPr | 2-Py | O | 135–137.5 | <0.1[c] |

[a]Dihydrochloride salt, broad melting range. (No. 143)
[b]See footnote b, Table 1.
[c]See footnote d, Table 1.
[d]2-py = 2-pyridyl

TABLE 13
Miscellaneous Compounds

| Comp. No. | DL | R₁ | R₃[a] | mp °C. | IC₅₀ (μM) |
|---|---|---|---|---|---|
| 197 | DL | 5-Cl | 2-Py | 180–183 | 0.22 |
| 198 | DL | 5-iPr | 2-Py | 150–151[b] | 0.12 |
| 199 | DL | 5-iPr | 4-Py | 145[b] | <0.3[c] |

TABLE 13-continued

| | | | | | |
|---|---|---|---|---|---|
| 200 | DL | 5-iPr | 3-Py | resin | <0.3[c] |

[a] 2-Py = 2-pyridyl, 4-Py = 4-Pyridyl, 3-Py = 3-Pyridyl
[b] Tosylate salt
[c] See footnote d, Table 1.

TABLE 14
Miscellaneous Compounds

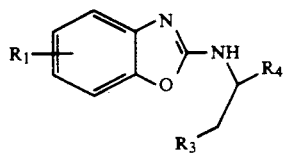

| Comp. No. | DL | $R_1$ | $R_4$ | $R_3$ | mp | $IC_{50}$ (μM) |
|---|---|---|---|---|---|---|
| 201 | L | 5-iPr | —CO$_2$Me | c | 143–146[a] | <1[b] |
| 202 | DL | 5-iPr | | d | Ph3Cl 168.5–170 | <0.1[b] |

[a] Hydrochloride Salt
[b] See footnote d, Table 1.
[c] 1-methyl-imidazol-4-yl
[d] 1-methyl-imidazol-2yl Antigen-induced bronchoconstriction in guinea pigs.

This model measures the ability of a compound to block the leukotriene component of antigen-induced bronchoconstriction. Male Hartley guinea pigs are actively sensitized to ovalbumin, pretreated with meptyramine and indomethacin (to block the histamine and cyclooxygenase metabolite componens respectively), and test compound (by aerosol administration). the guinea pigs are challenged with antigen (inhaled ovalbumin). Pulmonary function is measured by oscillatory mechanics as described by W. W. Wolyniec et. al. (Agents and Actions 1991, 34, $\frac{1}{2}$, 73). Results are expressed as percent inhibition or bronchoconstriction (impedance) in the test compound treated guinea pigs compared to placebo treated controls.

| Compound No. | Dose (Micrograms)* | N | % Inhibition |
|---|---|---|---|
| 51 | 274 | 6 | 86 |
| 56 | 95 | 6 | 43 |
| 81 | 308 | 6 | 64 |
| | 28 | 4 | 64 |
| | 2.8 | 10 | 61 |
| 165 | 274 | 7 | 85 |
| | 28 | 6 | 64 |
| | 5.6 | 4 | 0 |

*Refers to amount of test compound inhaled by guinea pig. Compounds administered by aerosolized freon/ethanol soltuion from metered dose inhaler.

What is claimed is:
1. A compound having the following formula:

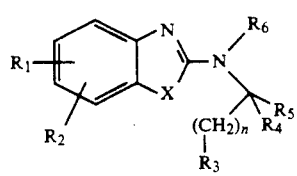

wherein
X is O or S
$R_1$ and $R_2$ are each, independent of one another, hydrogen; $C_1-C_6$ alkyl; halo ; $CF_3$; nitrile; $C_1-C_6$ alkoxy; —$CO_2R_7$ wherein $R_7$ is hydrogen or $C_1-C_6$ alkyl; $NO_2$; —C(O)NR$_8$R$_9$ wherein $R_8$ and $R_9$ are hydrogen, $C_1-C_3$ allyl or methoxy; —NR$_{10}$R$_{11}$ wherein $R_{10}$ and $R_{11}$ are hydrogen or $C_1-C_6$ alkyl; —C(O)R$_{12}$ wherein $R_{12}$ is $C_1-C_6$ alkyl; 'SO$_2$R$_{12}$, —NHC(O)R$_{12}$; —NHSO$_2$R$_{12}$; or —SO$_2$NR$_{13}$R$_{14}$ wherein $R_{13}$ and $R_{14}$ are hydrogen or $C_1-C_6$ alkyl;

$R_3$ is cyclohexyl or an optionally substituted phenyl ring wherein the substituents are selected from halo, $CF_3$, $C_1-C_4$ alkyl or $C_1-C_4$ alkoxy; —SO$_2$R$_{12}$; —NHC(O)R$_{12}$; —NHSO$_2$R$_{12}$; SO$_2$NR$_{13}$R$_{14}$; or $NO_2$; or $R_3$ may be a 2-, 3- or 4-pyridine ring; or $R_3$ may be a dialkylamine ($C_1-C_4$); or may be an alkyl ether, ($C_1-C_4$).

$R_4$ is 2-, 3-, or 4-pyridyl.
$R_5$ and $R_6$ are each, independent of one another, hydrogen or methyl and
n is an integer of b 0, 1 or 2, in racemic form, or the pure or substantially pure enantiomers thereof.

2. The compound as recited in claim 1 wherein
$R_1$ is the 5-position and is $C_1-C_3$ alkyl or halo
$R_2$ is hydrogen
$R_3$ is cyclohexyl
$R_4$ is 2-pyridyl or 3-pyridyl
$R_5$ is hydrogen
$R_6$ is hydrogen and n is 1.

3. The compound as recited in claim 1

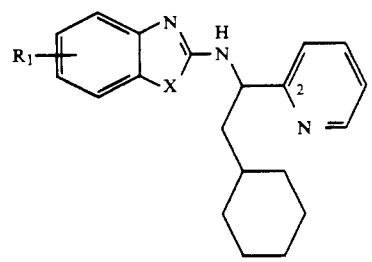

wherein X is oxygen and $R_1$ is 5-methyl.

4. The compound as recited in claim 3, the L-enantiomer thereof.

5. The compound as recited in claim 1

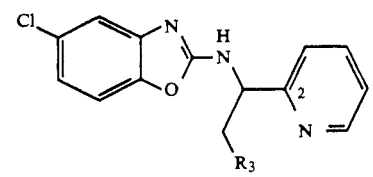

wherein $R_3$ is cyclohexyl.

6. The compound as recited in claim 1

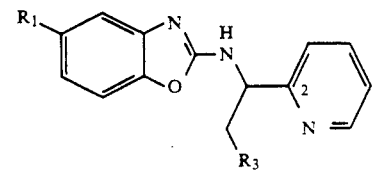

wherein
$R_1$ is isopropyl, methyl, chlor or methoxy and
$R_3$ is 4-fluorophenyl.

7. The compound as recited in claim 1

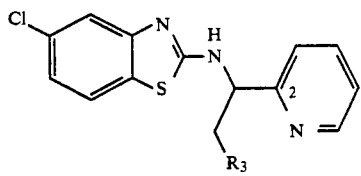

wherein

R₃ is 4-fluorophenyl or cyclohexyl.

8. A pharmaceutical composition of matter comprising a compound as recited in claim 1.

9. A method of treating disease in a warm-blooded animal through inhibition of leukotriene biosynthesis which comprises administering to the animal a leukotriene biosynthesis inhibiting amount of a compound as recited in claim 1.

10. A method of treating asthma in a warm-blooded animal which comprises administering to said animal a therapeutically effective amount of a compound as recited in claim 1.

* * * * *

UNITED STATES PATENT AND TRADEMARK OFFICE
CERTIFICATE OF CORRECTION

PATENT NO. : 5,296,486

DATED : March 22, 1994

INVENTOR(S) : Edward S. Lazer et al.

It is certified that error appears in the above-identified patent and that said Letters Patent is hereby corrected as shown below:

Title page, item [63],
Under "Related U.S. Application Data", the information should read as follows:

--Continuation-in-part of Ser. No. 764,591, September 24, 1991, abandoned.--

Signed and Sealed this

Twenty-eighth Day of May, 1996

Attest:

BRUCE LEHMAN

*Attesting Officer*     Commissioner of Patents and Trademarks